United States Patent [19]

May

[11] Patent Number: 5,552,415
[45] Date of Patent: Sep. 3, 1996

[54] METHOD OF INHIBITING ALZHEIMER'S DISEASE

[75] Inventor: Patrick C. May, Carmel, Ind.

[73] Assignee: Eli Lilly and Company, Indianapolis, Ind.

[21] Appl. No.: 171,387

[22] Filed: Dec. 21, 1993

[51] Int. Cl.$^6$ .................. A61K 31/445; A61K 31/38
[52] U.S. Cl. .................. 514/324; 514/317; 514/319; 514/422; 514/443
[58] Field of Search .................. 514/317, 319, 514/324, 443

[56] References Cited

U.S. PATENT DOCUMENTS

| | | | |
|---|---|---|---|
| 4,133,814 | 1/1979 | Jones et al. | 260/326.55 |
| 4,380,635 | 4/1983 | Peters | 546/202 |
| 4,418,068 | 11/1983 | Jones | 424/267 |
| 5,075,321 | 12/1991 | Schreiber | 514/317 |

FOREIGN PATENT DOCUMENTS

| | | |
|---|---|---|
| 4320896A1 | 6/1993 | Germany . |
| WO93/10113 | 5/1993 | WIPO . |
| WO93/1074 | 6/1993 | WIPO . |

OTHER PUBLICATIONS

Draper et al., "Effects of Raloxifene (LY139481 HCl) on Biochemical Markers of Bone and Lipid Metabolism i Healthy Postmenopausal Women", Hong Kong, Fourth Int'l Symp. on Osteoporosis, Mar. 29, 1993.

Bryant et al., "Protection from Bone Loss and Lowering of Serum Cholesterol in the Absence of Uterine Stimulation in Ovariectomized Rats", Am Soc. Bone & Min. Res., Tampa, Sep. 18–22, 1993.

Bryant et al., "Raloxifene is a Tissue Specific Estrogen Agonist", Am Soc. Bone & Min. Res., Tampa, Sep. 18–22, 1993.

Frolick et al., "In Vivo and In Vitro Metabolism of Raloxifene", Am. Soc. Bone & Min. Res., Tampa, Sep. 18–22, 1993.

Glasebrook et al., "Multiple Binding Sites for the Anti-estrogen Raloxifene", Am Soc. Bone & Min. Res., Tampa, Sep. 18–22, 1993.

Hock et al., "Combination of Raloxifene and Human Parathyoid Hormone 1–34; Increased Femur Bone Mass in Young Ovariectomized (OVX) Rats", Am. Soc. Bone & Min. Res., Tampa, Sep. 18–22, 1993.

Sato et al., "DEXA Analysis of Raloxifene Effects on the Bones From Ovariectomized Rats", Am. Soc. for Bone and Min. Res., Tampa, Sep. 18–22, 1993.

Yang et al., "Raloxifene an Anti–Estrogen, Simulates the Effects of Estrogen in Inhibiting Bone Resorption Through Regulating TGFB–3 Expression in Bone;".Am Soc for Bone and Min. Res., Tampa, Sep. 18–22, 1993.

Black et al., "Distinct, Structure–Related Profiles of Estrogenic and Anti-Estrogenic Activity in the Tamoxifen and LY117018 Series;" The Endocrine Society, Abstract 1982.

Black et al., "Uterine Bioassay of Tamoxifen, Trioxifene, and New Estrogen Antagonist (LY117018) in Rats and Mice," Life Sciences, 26:1980, 1453–1458.

Black et al., "Differential Interaction of Antiestrogens with Cytosol Estrogen Receptors," Molecular and Cellular Endocrinology, 22:1981, 95–103.

Black et al., "Evidence for Biological Action of the Antiestrogens LY117018 and Tamoxifen by Different Mechanisms," Endocrinology 109;1981, 987–989.

Black, L. J. "Biological Actions and Binding Properties of a New Estrogen Antagonist LY117018," In: Homone Antagonists, 129–82, 1982 (M. K. Agarwal ed.) Walter de Gruyter Co., Berlin New York.

Black et al., LY156758: A Unique Antiestrogen Displaying High Affinity for Estrogen Receptors, Negligible Estrogenic Activity and Near-Total Estrogen Antagonism in Vivo. Presented at the Fifth Annual San Antonio Breast Cancer Symposium, San Antonio, Texas, Nov. 5–6, 1982.

(List continued on next page.)

*Primary Examiner*—Shailendra Kumar
*Attorney, Agent, or Firm*—James J. Sales

[57] ABSTRACT

This invention encompasses methods for the inhibition of Alzheimer's Disease comprising administering to a human in need thereof an effective amount of a compound of Formula I

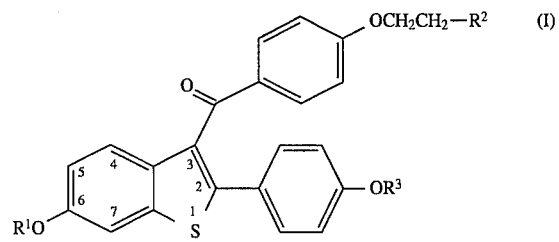

wherein R$^1$ and R$^3$ are independently hydrogen,

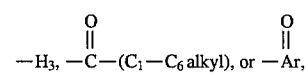

wherein Ar is optionally substituted phenyl; R$^2$ is selected from the group consisting of pyrrolidine, hexamethylenemino, and piperidino; or a pharmaceutically acceptable salt of solvate thereof.

The present invention also provides methods of increasing TGF-β expression in the brain, comprising administering to a human in need thereof an effective amount of a compound of formula 1.

The present invention also provides methods of inhibiting the β-amyloid peptide mediated neurotoxicity or inflammatory response associated with Alzheimer's Disease (AD) comprising administering to a human in need thereof an effective amount of a compound of formula 1.

4 Claims, No Drawings

OTHER PUBLICATIONS

Black et al., The Antiestrogenic Action of LY139481: Species Uniformity Duration of Action and Kinetics of 3H–LY139481 Distribution In Vivo. Sixth–fifth Annual Meeting of the Endocrine Society, San Antonio, Texas, Jun. 8–10, 1983, abs. 93.

Black et al., Antagonism of Estrogen Action with a New benzothiophene Derived Antiestrogen, Life Sciences, 32:1983. 1031–1036.

Black et al., The Relationship of the Antiestrogenic Efficacy of LY156758 to its Pharmacokinetics and Metabolism Following Oral Administration to Adult Ovariectomized Rats, Seventh International Congress of Endocrinology, Quebec City, Canada, Jul. 1–7, 1984, abs. 323.

Black et al., Synthesis and Antiestrogenic Activity of [3,4–Dihydro–2(4–methoxyphenyl)–1–napthalenyl] [4–[2–pyrrolidinyl) ethoxy]–phenyl] methanone, methanesulfonic acid salt, Journal of Medicinal Chemistry 22;1979, 962–966.

Black et al., Antiestrogens 2. Structure Activity Studies in a Series of 3–Aroyl–2–arylbenzo[b]thiophene Derivatives Leading to [6–Hydroxy–2–(4–hydroxyphenyl)benzo[b]thien–3–yl][4–[2–(1–piperidinyl)ethoxy]–phenyl]methanone Hydrochloride (LY156758), a Remarkably Effective Estrogen Antagonist with Only Minimal Intrinsic Estrogenicity, J. Med. Chem. 27(8), 1984, 1057–1066.

"New Alzheimer's Therapy Suggested", *Science*, 260, 1719–1720 (Jun. 18, 1993).

"Women on Estrogen Appear at Less Risk of Alzheimer's", Indianapolis Star, Nov. 10, 1993.

Knabbe et al., Evidence that Transforming Growth Factor–$\beta$ Is A Hormonally Regulated Negative Growth Factor in Human Breast Cancer Cells, Cell, vol. 48, No. 3, pp. 417–428 (1987).

Chao, C. C. et al., Transforming Growth Factor–$\beta$ Protects Human Neurons Against $\beta$–Amyloid–Induced Injury, Degennerative Disease, vol. 19, p. 1251 (1993).

Yang et. al, J. Bone and Mineral Research, vol. 8, No. 51, Aug. 1993, p. S118.

METHOD OF INHIBITING ALZHEIMER'S DISEASE

BACKGROUND OF THE INVENTION

Alzheimer's Disease (AD) is a degenerative brain disorder characterized clinically by progressive loss of memory, cognition, reasoning, judgment and emotional stability that gradually leads to profound mental deterioration and ultimately death. AD is a common cause of progressive mental failure (dementia) in aged humans and is believed to represent the fourth most common medical cause of death in the United States. AD has been observed in varied races and ethnic groups worldwide and presents a major present and future public health problem. The disease is currently estimated to affect about two to three million individuals in the United States alone. To date, AD has proven to be incurable.

The brains of individuals with AD exhibit neuronal degeneration and characteristic lesions variously referred to as amyloidogenic plaques, vascular amyloid angiopathy, and neurofibrillary tangles. Large numbers of these lesions, particularly amyloidogenic plaques and neurofibrillary tangles, are generally found in several areas of the human brain important for memory and cognitive function in patients with AD. Smaller numbers of these lesions in a more restricted anatomical distribution are found in the brains of most aged humans who do not have clinical AD. Amyloidogenic plaques and vascular amyloid angiopathy also characterize the brains of individuals with Trisomy 21 (Down's Syndrome) and Hereditary Cerebral Hemorrhage with Amyloidosis of the Dutch-Type (HCHWA-D). At present, a definitive diagnosis of AD usually requires observing the aforementioned lesions in the brain tissue of patients who have died with the disease or, rarely, in small biopsied samples of brain tissue taken during an invasive neurosurgical procedure.

Several lines of evidence indicate that progressive cerebral deposition of particular amyloidogenic proteins, β-amyloid proteins, (βAP), play a seminal role in the pathogenesis of AD and can precede cognitive symptoms by years or decades. See, *Selkoe*, (1991) Neuron 6:487. Recently, it has been shown that βAP is released from neuronal cells grown in culture and is present in cerebrospinal fluid (CSF) of both normal individuals and AD patients. See, *Seubert et al.*, (1992) Nature 359:325–327.

A possible correlation to the plaque pathology has been developed by several groups demonstrating the direct βAP neurotoxicity toward, cultured neurons. Direct neurotoxicity of βAP was recently reported to be attenuated by co-treatment with TGF-β (Chao et al., *Soc. Neurosci. Abs.*, 19: 1251 (1993)).

More recently, in addition to the direct neurotoxicity, an inflammatory response in the AD brain, perhaps elicited by βAP, also contributes to the pathology of the disease. A limited clinical trial with the NSAID indomethacin exhibited a retardation in the progression of Alzheimer's dementia (Rogers et al., Science, 260:1719–1720 (1993)).

Despite the progress that has been made in understanding the underlying mechanisms of AD, there remains a need to develop compositions and methods for treatment of these diseases. Treatment methods could advantageously be based on drugs which are capable of increasing TGF-β expression in the brain, thus ameliorating the β-amyloid peptide mediated neurotoxicity and inflammatory response associated with AD.

SUMMARY OF THE INVENTION

This invention encompasses methods for the inhibition of Alzheimer's disease, which method comprises administering to a human in need thereof an effective amount of a compound of formula I

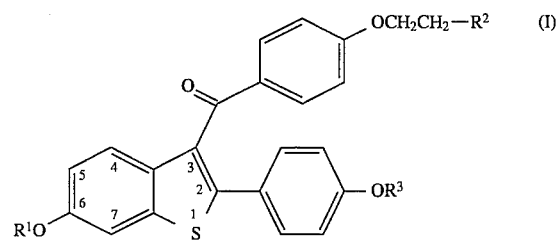

wherein $R^1$ and $R^3$ are independently hydrogen,

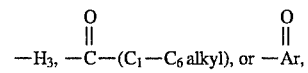

wherein Ar is optionally substituted phenyl;
$R^2$ is selected from the group consisting of pyrrolidino, hexamethylenemino, and piperidino; or a pharmaceutically acceptable salt of solvate thereof.

The present invention also provides a method of increasing TGF-β expression in the brain, comprising administering to a human in need thereof an effective amount of a compound of formula 1.

The present invention also provides a method of inhibiting the β-amyloid peptide mediated neurotoxicity and inflammatory response associated with Alzheimer's Disease (AD) comprising administering to a human in need thereof an effective amount of a compound of formula 1.

DETAILED DESCRIPTION OF THE INVENTION

The current invention concerns the discovery that a select group of benzothiophenes, those of formula I, are useful for inhibiting the effects of Alzheimer's Disease, and in particular the compounds are believed to inhibit the inflammatory response associated with the disease by increasing TGF-β expression in the brain. The invention encompasses uses practiced by administering to a human in need thereof a dose of a compound of formula 1 or a pharmaceutically acceptable salt or solvate thereof effective to inhibit Alzheimer's Disease. The methods include both therapeutic and prophylactic administration.

The term "inhibit" includes its generally accepted meaning which includes prohibiting, preventing, restraining, and slowing, stopping, or reversing progression, severity, or a resultant symptom or effect.

The term "effective amount" means the amount of compound necessary to inhibit Alzheimer's Disease or any of its symptoms, inhibit β-amyloid peptide mediated neurotoxicity or the inflammatory response associated with Alzheimer's Disease, or increase TGF-β expression in the brain, as the case may be.

Generally, the compound is formulated with common excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms and the like.

The compounds used in the methods of the current invention can be made according to established and analogous procedures, such as those detailed in U.S. Pat. Nos. 4,133,814, 4,418,068, and 4,380,635 all of which are incorporated by reference herein. In general, the process starts with a benzo[b]thiophene having a 6-hydroxyl group and a 2-(4-hydroxyphenyl) group. The starting compound is protected, alkylated or acylated, and deprotected to form the formula I compounds. Examples of the preparation of such compounds are provided in the U.S. patents discussed above, and in the examples in this application. Optionally substituted phenyl includes phenyl and phenyl substituted once or twice with $C_1$–$C_6$ alkyl, $C_1$–$C_4$ alkoxy, hydroxy, nitro, chloro, fluoro, or tri(chloro or fluoro)methyl.

Included in this invention is the compound raloxifene, below:

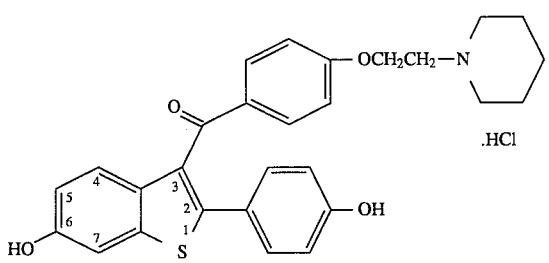

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferable salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides and carbonates, as well as aliphatic and aromatic amines, aliphatic diamines and hydroxy alkylamines. Bases especially useful in the preparation of addition salts include ammonium hydroxide, potassium carbonate, sodium bicarbonate, calcium hydroxide, methylamine, diethylamine, ethylene diamine, cyclohexylamine and ethanolamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agaragar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

Compounds of Formula I can be administered for prophylactic and/or therapeutic treatment of Alzheimer's Disease. In therapeutic applications, the compounds are administered to a host already suffering from a disease.

For prophylactic applications, the compounds of formula I are administered to a host susceptible to Alzheimer's Disease, but not necessarily already suffering from such disease. Such hosts may be identified by genetic screening and clinical analysis, as described in the medical literature, see e.g., Goate, *Nature*, 349:704–706 (1991). A preferred group for receiving compounds of the invention, either for prophylactic or therapeutic reasons, are post-menopausal women. (see e.g., Paganini-Hill, *Soc NeuroSci Abs*, 19, 1046).

The particular dosage of a compound of formula I according to this invention will depend upon the severity of the condition, the route of administration, and related factors that will be decided by the attending physician. Generally, accepted and effective daily doses will be from about 0.1 to about 1000 mg/day, and more typically from about 50 to about 200 mg/day. Such dosages will be administered to a subject in need of treatment from once to about three times each day, or more often as needed, for a period of time sufficient to inhibit the effects of Alzheimer's Disease or its symptoms.

Frequently, it will be desirable or necessary to introduce the pharmaceutical compositions directly or indirectly to the brain. Direct techniques usually involve placement of a drug delivery catheter into the host's ventricular system to bypass the blood-brain barrier. Indirect techniques, which are generally preferred, involve formulating the compositions to provide for drug latentiation by the conversion of hydrophilic drugs into lipid-soluble drugs. Latentiation is generally achieved through blocking of the hydroxyl, carboxyl, and primary amine groups present on the drug to render the drug more lipid soluble and amenable to transportation across the blood-brain barrier. Alternatively, the delivery of hydrophilic drugs can be enhanced by intra-arterial infusion of hypertonic solutions which can transiently open the blood-brain barrier.

It is usually preferred to administer a compound of formula I in the form of an acid addition salt, as is customary in the administration of pharmaceuticals bearing a basic group, such as the piperidino ring. For such purposes the following dosage forms are available.

FORMULATIONS

In the formulations which follow, "Active ingredient" means a compound of formula I.

Formulation 1: Gelatin Capsules

Hard gelatin capsules are prepared using the following:

| Ingredient | Quantity (mg/capsule) |
| --- | --- |
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of specific capsule formulations of the compound raloxifene that have been made include those shown below:

| Ingredient | Quantity (mg/capsule) |
| --- | --- |
| Formulation 2: Raloxifene capsule | |
| Raloxifene | 1 |
| Starch, NF | 112 |
| Starch flowable powder | 225.3 |
| Silicone fluid 350 centistokes | 1.7 |
| Formulation 3: Raloxifene capsule | |
| Raloxifene | 5 |
| Starch, NF | 108 |
| Starch flowable powder | 225.3 |
| Silicone fluid 350 centistokes | 1.7 |
| Formulation 4: Raloxifene capsule | |
| Raloxifene | 10 |
| Starch, NF | 103 |
| Starch flowable powder | 225.3 |
| Silicone fluid 350 centistokes | 1.7 |
| Formulation 5: Raloxifene capsule | |
| Raloxifene | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

| Formulation 6: Tablets | |
| --- | --- |
| Ingredient | Quantity (mg/tablet) |
| Active ingredient | 0.1–1000 |
| Cellulose, microcrystalline | 0–650 |
| Silicon dioxide, fumed | 0–650 |
| Stearate acid | 0–15 |

The components are blended and compressed to form tablets.

Alternatively, tablets each containing 0.1–1000 mg of active ingredient are made up as follows:

| Formulation 7: Tablets | |
| --- | --- |
| Ingredient | Quantity (mg/tablet) |
| Active ingredient | 0.1–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 mL dose are made as follows:

| Formulation 8: Suspensions | |
| --- | --- |
| Ingredient | Quantity (mg/5 ml) |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

ASSAYS

Experimental Design

For Assay 1 and 2, the following experimental design is provided.

Amylins may be purchased from Bachem, Inc. (Torrance, California), Peninsula Laboratories, Inc. (Belmont, California), Sigma Chemicals (St. Louis, Mo.) or may be synthesized as described infra. Amyloid-β(1-40) and reverse β-amyloid peptide(40-1) may be purchased from Bachem, Inc. $β_2$-microglobulin may be purchased from Sigma Chemicals (St. Louis, Mo.).

Stock solutions of peptides (1 mM) are freshly prepared in pyrogen-free sterile water and diluted to the indicated concentrations in defined culture media. Rat hippocampal cultures (10–14 days in vitro) are treated with peptides or vehicle for four days. The viability of the rat cortical cultures is visually assessed by phase contrast microscopy and quantified by measuring lactate dehydrogenase (LDH) released into the culture media.

Assay 1

Primary rat hippocampal neurons are cultured in vitro with standard cell culture techniques. Amyloid-beta (Aβ) peptide is added to cultured cells at a normally toxic concentration of 25–50 μM. After 4 days of treatment, viability is assessed by measurement of lactate dehydrogenase (LDH) released into culture medium. Lactate dehydrogenase (LDH) is measured in 20 μl aliquots of conditioned defined-DMEM using a standard 340 nm kinetic LDH assay (Sigma Catalog Number #228-20) in a 96 well format. Assays are performed at 37° C. in a PC-driven EL340 Microplate Biokinetics plate reader (Bio-Tek Instruments) using Delta Soft II software (v. 3.30B, BioMetallics, Inc.) for data analysis. Quality control standards containing normal and elevated levels of serum LDH (for example, Sigma Enzyme Controls 2N and 2E) are run with every assay. Results are expressed as units of LDH/L where 1 unit is defined as the amount of enzyme that will catalyze the formation of 1 micromole of nicotinamide adenine dinucleotide per minute under conditions of the assay. For protection studies, a compound of formula 1 is added to cultures prior to and/or concurrently with the amyloid-β treatment.

Activity of the compounds of formula 1 is illustrated by a decrease in LDH released into the media (a neurotoxic indicator), as compared to control.

Assay 2

Between five and fifty rats are subjected to 15 minutes of four vessel occlusion to induce global ischemia. A compound of the invention is administered to experimental and control animals prior to, concurrent with and/or up to several hours after 15 minutes of occlusion. Animals are sacrificed 3 days after the ischemic insult and neuronal damage in the hippocampus and striatum is then visually assessed by standard histologic techniques.

Activity of the compounds of formula 1 is illustrated by a decrease in neuronal damage.

Assay 3

Five to fifty women are selected for the clinical study. The women are post-menopausal, i.e., have ceased menstruating for between 6 and 12 months prior to the study's initiation, have been diagnosed with early stage Alzheimer's Disease (AD), are expected to have worsening symptoms of AD within the study period, but are in good general health otherwise. The study has a placebo control group, i.e., the women are divided into two groups, one of which receives the active agent of this invention and the other receives a placebo. The patients are benchmarked as to memory, cognition, reasoning, and other symptoms associated with AD. Women in the test group receive between 50–200 mg of the active agent per day by the oral route. They continue this therapy for 6–36 months. Accurate records are kept as to the benchmarked symptoms in both groups and at the end of the study these results are compared. The results are compared both between members of each group and also the results for each patient are compared to the symptoms reported by each patient before the study began. Activity of the test drug is illustrated by an attenuation of the typical cognitive decline and/or behavioral disruptions associated with AD.

Utility of the compounds of formula I is evidenced by activity in at least one of the above assays.

We claim:

1. A method of increasing TGF-β expression in the brain comprising administering to a human in need thereof an effective amount of a compound of Formula I

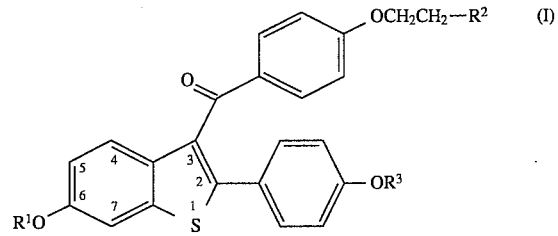

wherein $R^1$ and $R^3$ are independently hydrogen,

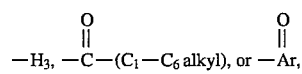

wherein Ar is optionally substituted phenyl;

$R^2$ is selected from the group consisting of hexamethyleneimino, and piperidino; or a pharmaceutically acceptable salt of solvate thereof.

2. The method of claim 1, wherein said administration is prophylactic.

3. The method of claim 1 wherein said human is a post-menopausal female.

4. The method of claim 1 wherein said compound

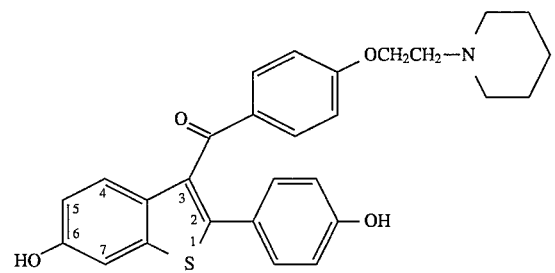

or its hydrochloride salt.

* * * * *